United States Patent
Takeda et al.

(10) Patent No.: US 9,448,228 B2
(45) Date of Patent: Sep. 20, 2016

(54) CELL ANALYZING APPARATUS AND CELL ANALYZING METHOD

(71) Applicant: NIHON KOHDEN CORPORATION, Tokyo (JP)

(72) Inventors: Sunao Takeda, Tokyo (JP); Takahiro Shioyama, Tokyo (JP); Akane Suzuki, Tokyo (JP); Yo Kato, Tokyo (JP); Nae Hinata, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 402 days.

(21) Appl. No.: 13/917,534

(22) Filed: Jun. 13, 2013

(65) Prior Publication Data

US 2013/0337501 A1    Dec. 19, 2013

(30) Foreign Application Priority Data

Jun. 15, 2012 (JP) ................. 2012-135792

(51) Int. Cl.
| | |
|---|---|
| G01N 33/48 | (2006.01) |
| G01N 33/50 | (2006.01) |
| G06K 9/00 | (2006.01) |
| G06K 9/52 | (2006.01) |
| G06F 19/00 | (2011.01) |

(52) U.S. Cl.
CPC ....... G01N 33/5091 (2013.01); G06K 9/00127 (2013.01); G06K 9/00147 (2013.01); G06K 9/522 (2013.01); *G06F 19/345* (2013.01)

(58) Field of Classification Search
CPC .................................................. G01N 33/5091
USPC ........................................................ 702/21
See application file for complete search history.

(56) References Cited

U.S. PATENT DOCUMENTS 5,633,945 A * 5/1997 Kamentsky ............... C12Q 1/68
                                                                382/129
2012/0052491 A1    3/2012 Shioyama et al.

FOREIGN PATENT DOCUMENTS

| JP | 10-508690 A | 8/1998 |
| JP | 2012-47594 A | 3/2012 |
| WO | 96/11448 A1 | 4/1996 |

OTHER PUBLICATIONS

Baer et al. "High Frequency of Immunophenotype Changes in Acute Myeloid Leukemia at Relapse: Implications for Residual Disease Detection (Cancer and Leukemia Group B Study 8361", Blood (2001) vol. 97, No. 11, pp. 3574-3580.*
Takeda et al., "Flow Cytometry as a Diagnostic Method for Colorectal Cancer," 2012 Annual International Conference of the IEEE Engineering in Medicine and Biology Society, (Aug. 28, 2012-Sep. 1, 2012).
Japanese Office Action for the related Japanese Patent Application No. 2012-135792 dated Nov. 4, 2015.
Nae Hinata et al.; "Research on a new cancer diagnosis method by applying FFT to the DNA ploidy analysis"; Biomedical Engineering, Japan; Apr. 10, 2013; vol. 51, No. 2; pp. 103-111.
Tomoko Arai et al.; "Basic review of the automatic blood analysis device Proto 3 applying optical Fourier conversion technology (2nd edition)—Proto 3: Evaluation with clinical specimens with the version 2.00"; Journal of the Japanese Society for Laboratory Hematology, Japan; Feb. 28, 2005; vol. 6, No. 1; pp. 53-61.
Yutaka Nagai et al.; "Development of the automatic blood analysis device Proto 3 applying optical Fourier conversion technology (1st version)—Assay of Nuclear chromatin structure analysis using spatial frequency information"; Journal of the Japanese Society for Laboratory Hematology, Japan; Nov. 30, 2003; vol. 4, No. 3; pp. 377-383.

* cited by examiner

*Primary Examiner* — Jerry Lin
(74) *Attorney, Agent, or Firm* — Pearne & Gordon LLP (57) ABSTRACT

A cell analyzing apparatus includes: a histogram acquirer which is configured to perform measurement of a number of nuclear stained cells, and which, by using a result of the measurement, is configured to acquire a histogram indicating a fluorescence intensity; and an analysis controller which is configured to apply frequency analysis on data of the histogram acquired by the histogram acquirer, and which is configured to determine existence/nonexistence of cancer cells based on a result of the frequency analysis.

6 Claims, 13 Drawing Sheets

| CASE | AUC NORMAL | AUC CANCER | RIPPLE NORMAL | RIPPLE CANCER |
|---|---|---|---|---|
| 1 | 21 | 20 | 1 | × |
| 2 | 38 | 20 | - | × |
| 3 | 32 | 17 | ○ | × |
| 4 | 42 | 25 | - | ○ |
| 5 | 35 | 27 | - | × |
| 6 | 24 | 21 | ○ | 1 |
| 7 | 53 | 23 | - | × |
| 8 | 29 | 17 | ○ | × |
| 9 | 34 | 16 | - | × |
| 10 | 25 | 13 | 1 | V |
| 11 | 29 | 12 | 1 | V |
| 12 | 51 | 14 | - | V |
| 13 | 33 | 19 | - | × |
| 14 | 30 | 21 | 1 | ○ |
| 15 | 41 | 24 | - | × |
| 16 | 29 | 10 | 1 | × |
| 17 | 47 | 26 | - | 1 |
| 18 | 40 | 32 | - | 1 |
| 19 | 45 | 30 | - | × |
| 20 | 36 | 25 | - | 1 |
| 21 | 33 | 22 | - | × |
| 22 | 37 | 29 | - | × |
| 23 | 51 | 18 | - | × |
| 24 | 28 | 21 | ○ | × |
| 25 | 19 | 11 | ○ | V |
| 26 | 15 | 12 | × | V |
| max | 53 | 32 | | |
| min | 15 | 10 | | |

|  |  | NORMAL | CANCER |
|---|---|---|---|
| 32 < AUC | ..."-" | 15/26 | |
| 15 ≤ AUC ≤ 32 | NO RIPPLE ..."○" | 5/26 | 2/26 |
| | ONE RIPPLE ..."1" | 5/26 | 4/26 |
| | MANY RIPPLES ..."×" | 1/26 | 15/26 |
| AUC < 15 | ..."V" | | 5/26 |

FIG. 10 (b)

| NORMAL | | CANCER | |
|---|---|---|---|
| 20/26 | -, ○ | 20/26 | V, × |
| 1/26 | × | 2/26 | ○ |
| 5/26 | 1 | 4/26 | 1 |

"1": DIAGNOSIS OF SUSPICION OF CANCER
"○": DIAGNOSIS OF NORMAL
"×": DIAGNOSIS OF CANCER

CELL ANALYZING APPARATUS AND CELL ANALYZING METHOD

CROSS-REFERENCE TO RELATED APPLICATION(S)

This application is based upon and claims the benefit of priority from prior Japanese patent application No. 2012-135792, filed on Jun. 15, 2012, the entire contents of which are incorporated herein by reference.

BACKGROUND

The presently disclosed subject matter relates to a cell analyzing apparatus and a cell analyzing method which correctly distinguish between normal and cancer tissues.

After a pathological specimen is prepared, a pathological diagnosis on a tissue slice is performed by a cytotechnologist or a pathologist. A skilled technique is required for preparing a specimen or performing a diagnosis by a cytotechnologist or a pathologist, and there is a possibility that a difference may be produced in the diagnosis result depending on the difference in technique. In the period from extraction of a tissue to diagnosis, procedures such as tissue fixation, slice preparation, and staining are necessary, and a cytotechnologist, a pathologist, or the like is restrained for a predetermined time period. Therefore, procedures which are to be performed before a diagnosis are requested to be automatized.

Moreover, a determination whether a tissue extracted during an operation is a tumor tissue or a normal tissue is required depending on the portion of a tumor or the operative method. In the determination, a rapid diagnosis due to cytoscreening or a frozen slice is performed. As compared with a usual pathological analysis, however, higher skilled technique and diagnosis accuracy are requested. If an apparatus which performs objectively and rapidly a diagnosis whether tissue extracted during an operation is tumor (cancer cells) or not is developed, such an apparatus seems to be very useful for a pathologist.

Therefore, for example, JP-A-2012-047594 discloses an apparatus and method of analyzing cells in which cells that are isolated and nuclear stained are measured to acquire a histogram, of the fluorescence intensity, the number of strong-area cells that are distributed in an area where the fluorescence intensity is stronger than normal cells is obtained from data of the histogram, and the malignancy grade of cancer is determined based on the number of strong-area cells and the histogram.

According to the apparatus and method of analyzing cells disclosed in JP-A-2012-047594, it is possible to determine the malignancy grade of cancer based on a histogram and the number of cells that are distributed in an area where the fluorescence intensity is stronger in the histogram. However, it is requested to perform more rapidly and accurately the determination of cancerous cells.

SUMMARY

The presently disclosed subject matter may provide a cell analysing apparatus and a cell analysing method which can distinguish cancerous cells more accurately and rapidly.

The cell analyzing apparatus may comprise: a histogram acquirer which is configured to perform measurement of a number of nuclear stained cells, and which, by using a result of the measurement, is configured to acquire a histogram indicating a fluorescence intensity; and an analysis controller which is configured to apply frequency analysis on data of the histogram acquired by the histogram acquirer, and which is configured to determine existence/nonexistence of cancer cells based on a result of the frequency analysis.

The frequency analysis may be a Fast Fourier Transform.

The analysis controller may determine the existence/nonexistence of the cancer cells by comparing an area, under a curve of a waveform which is obtained from the result of the frequency analysis, with a predetermined threshold.

The analysis controller may determine the existence/nonexistence of the cancer cells depending on whether or not a waveform which is obtained from the result of the frequency analysis ripples in a spatial frequency.

The analysis controller may determine the existence/nonexistence of the cancer cells depending on whether or not a waveform which is obtained from the result of the frequency analysis steeply attenuates in a direction toward a higher frequency in a low spatial frequency region.

The analysis controller may comprehensively determine a comparison between an area under a curve of a waveform which is obtained from the result of the frequency analysis, and a predetermined threshold, existence/nonexistence of a ripple in a spatial frequency, and existence/nonexistence of steep attenuation in a direction toward a higher frequency in a low spatial frequency region, thereby determining the existence/nonexistence of the cancer cells.

The predetermined threshold may be a value of the area under the curve, which is obtained from normal cells of a living body.

The cell analyzing method may comprise: performing measurement of a number of nuclear stained cells, and, by using a result of the measurement, acquiring a histogram, indicating a fluorescence intensity; applying frequency analysis on data of the acquired histogram; and determining existence/nonexistence of cancer cells based, on a result of the frequency analysis.

The frequency analysis may be a Fast Fourier Transform.

BRIEF DESCRIPTION OF THE DRAWINGS

FIGS. 4(a) and 4(b) are views which show an example of a result of a process of analyzing cancer cells, and in which

FIGS. 5(a) and 5(b) are views which show an example of a result of a process of analyzing cancer cells, and in which

FIGS. 6(a) and 6(b) are views which show an example of a result of a process of analyzing cancer cells, and in which FIG. 6(a) shows histograms, and FIG. 6(b) snows a result of a frequency analysis of the histograms.

FIGS. 7(a), 7(b) and 7(c) are views which show an example of a result of a process of analyzing cancer cells, and in which

FIGS. 9(*a*), 9(*b*) and 9(*c*) are views which show an example of a result of analyzing cancer cells, and in which FIG. 9(*a*) snows a histogram, FIG. 9(*b*) shows histograms in which the cell number of the ordinate of FIG. 9(*a*) is normalized, and FIG. 9(*c*) shows a result of a frequency analysis of the histograms of FIG. 9(*b*).

FIGS. 10(*a*) and 10(*b*) are tables in which FIG. 10(*a*) is a table showing measurement data of the AUC (Area Under the Curve) and ripple of an FFT pattern, and FIG. 10(*b*) is a table showing diagnosis results based on the data of FIG. 10(*a*).

DETAILED DESCRIPTION OF EXEMPLARY EMBODIMENTS

Hereinafter, an embodiment of the apparatus and method of analyzing cells of the presently disclosed subject matter will be described with reference to the accompanying drawings.

Figure 1:
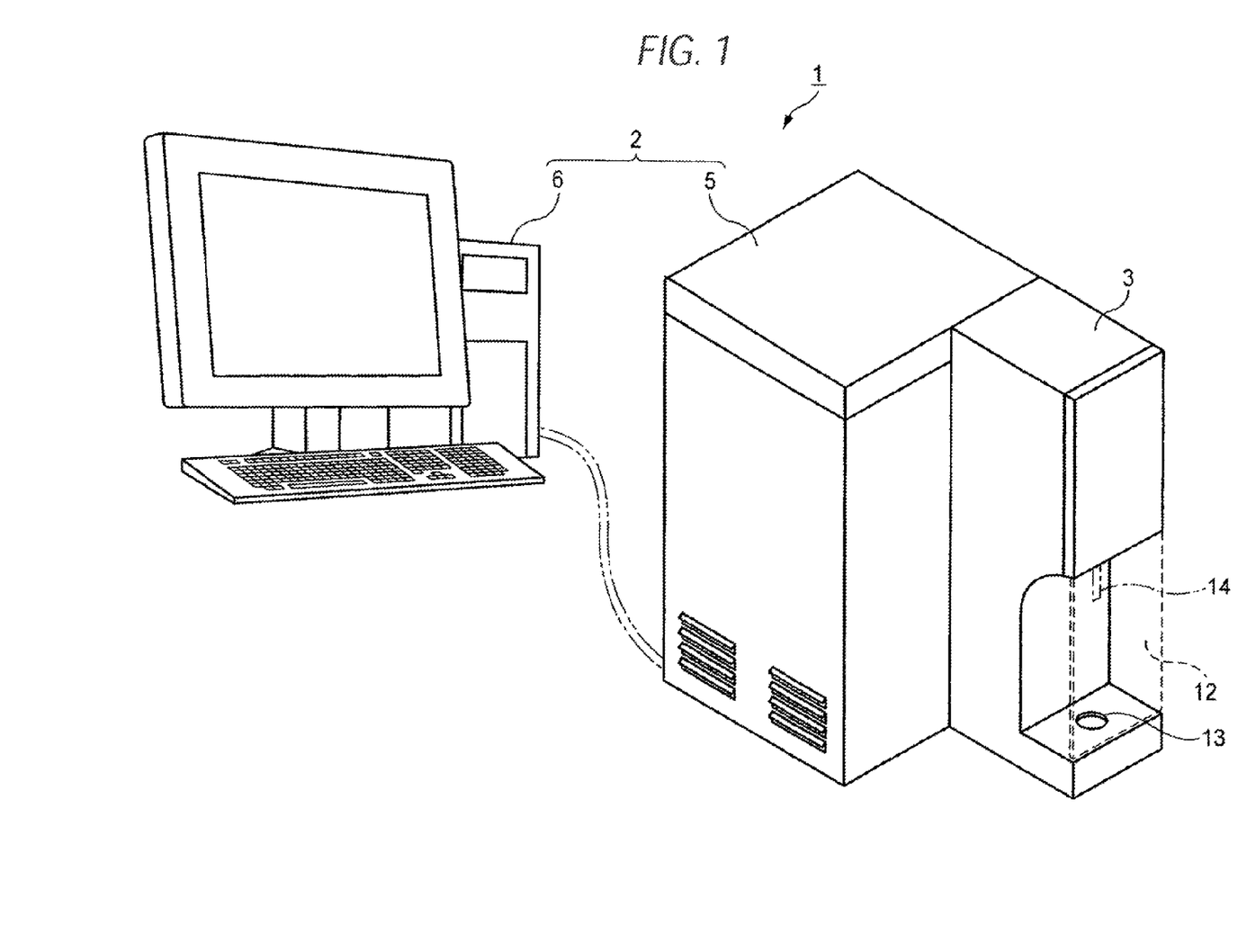
FIG. 1 is a diagram of a cell analysis system which includes an embodiment of the apparatus for analyzing cells of the presently disclosed subject matter.

FIG. 1 shows a cell analysis system 1 tor analyzing cells. The cell analysis system 1 includes a cell analyzing apparatus 2, a cell pre-processing apparatus 3, and a cell isolation device 4 (see FIG. 2) which is set in the cell pre-processing apparatus 3. The cell analyzing apparatus 2 includes a flow cytometer 5 and a personal computer (PC) 6.

Figure 2:
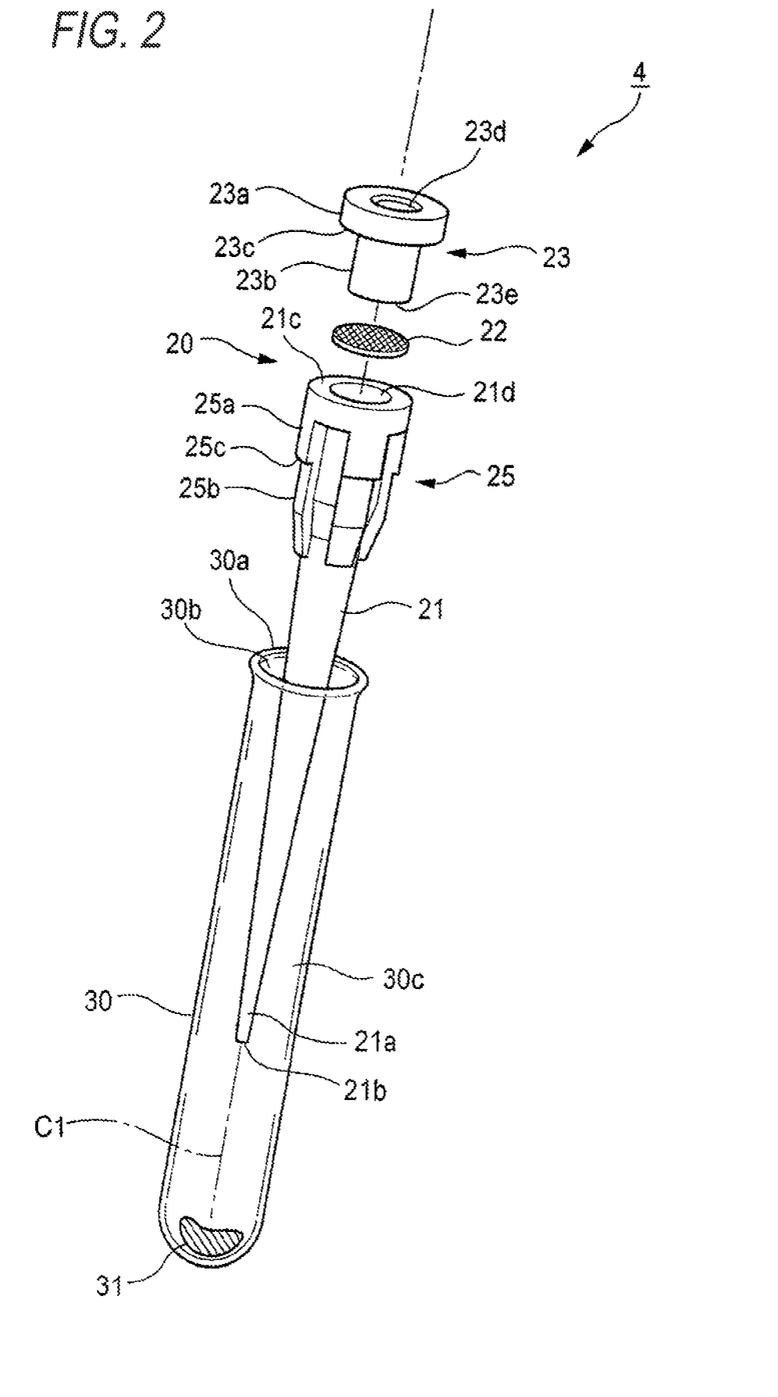
FIG. 2 is an exploded perspective view showing an example of a cell isolation device.

The cell isolation device 4 is a tubular container into which the tissue to be analyzed is poured. The cell isolation device 4 is set in the cell pre-processing apparatus 3 in a state where the device is inserted into a container 30 in which a reagent is to be contained. The cell pre-processing apparatus 3 is an apparatus for performing a pipetting process of introducing and withdrawing a cell treating chemical, a phosphate buffer solution, and a tissue into and from the cell isolation device 4 through a nozzle.

The flow cytometer 5 (an example of a histogram acquirer) is an apparatus which is to be used in flow cytometry. Flow cytometry means a technique in which fine particles are dispersed in a fluid, and individual particles are optically analyzed while the fluid, (suspending solution) is flown. The fine particles may be selectively recovered. In the embodiment of the flow cytometer 5 measures the number of cells which are nuclear stained, and, by using a result of the measurement, acquires a histogram showing the fluorescence intensity.

The PC 6 is an apparatus which performs a frequency analysis on data of the histogram acquired by the flow cytometer 5. Hereinafter, the PC 6 is often referred to also as an analysis controller 6. Here, the frequency analysis is a FFT (Fast Fourier Transform), a MEM (Maximum Entropy Method), an AR (Auto Regressive) model, an ARMA (Auto Regressive-Moving Average) model, an STFT (Short Time Fourier Transform), a Wavelet transform, a Wigner distribution, or the like.

The flow cytometer 5 and the PC 6 may be configured so as not to be formed as independent apparatuses, and the flow cytometer 5 may have the functions of the flow cytometer 5 and the PC 6.

FIG. 2 shows the cell isolation device 4 in an exploded state. The cell isolation device 4 includes a pipette member 20, and a container 30. The both components are formed by a resin material or the like which is noncytotoxic.

The pipette member 20 includes a body 21, a filter 22 (filter member), and a lid member 23.

The body 21 is a hollow cylindrical member in which a tip end portion 21*a* has a tapered shape. An opening 21*b* is formed in the tip end (lower end) of the body 21, and an opening 21*d* is formed in the upper end surface 21*c*. The openings 21*b*, 21*d* communicate with each other through a passage which is formed inside the body 21.

A holding member 25 is disposed in an upper end portion of the body 21. The holding member 25 has a large-diameter portion 25*a* and a small-diameter portion 25*b*. A step 25*c* is defined in the interface between the large-diameter portion 25*a* and the small-diameter portion 25*b*. The large-diameter portion 25*a* includes the upper end surface 21*c*.

The filter 22 is formed by a material which is noncytotoxic, and has mesh openings which allow a liquid containing isolated cells (cells in which nuclei are isolated) to pass therethrough. In the embodiment, a nylon mesh having mesh openings of 50 μm is used as the filter 22, and adhered or welded to the lid member 23 so as to cover an opening 23*e* of the lower end surface of the lid member 23.

The lid member 23 is a cylindrical member having a large-diameter portion 23*a* and a small-diameter portion 23*b*. A step 23*c* is defined in the interface between the large-diameter portion 23*a* and the small-diameter portion 23*b*. An opening 23*d* is formed in the upper end surface including the large-diameter portion 23*a*, and an opening 23*e* is formed in the lower end surface including the small-diameter portion 23*b*. The openings 23*d*, 23*e* communicate with each other through a passage which is formed inside the lid member 23.

The filter 22 and the small-diameter portion 23*b* of the lid member 23 are inserted into the opening 21*d* to be attached to the body 21, and the step 23*c* of the lid member 23 is adhered or welded to the upper end surface 21*c* of the body 21. In this state, the passage of the body 21 and that of the lid member 23 communicate with each other through the filter 22.

The container 30 is a cylindrical member which has an opening 30*b* in the upper end surface 30*a*, and in which a lower end portion is configured as a round bottom. The container 30 is transparent so that the hollow internal space 30*c* is visible. The internal space 30*c* communicates with the opening 30*b*.

The pipette member 20 is attached to the container 30 in which the tissue and the cell treatment solution are accommodated in the internal space 30*c*. The body 21 of the pipette member 20 is inserted from the opening 30*b* of the container 30 into the internal space 30*c* until the upper end surface 30*a* of the container 30 abuts against the step 25*c* of the holding member 25. The tip end (opening 21*b*) of the body 21 is placed on the central axis C1 of the container 30, and opposed to the bottom of the internal space 30*c* via a constant gap. The loaded tissue is placed between the tip end of the body 21 and the bottom of the internal space 30*c*. The tip end portion 21*a* of the body 21 is immersed in the loaded cell treatment solution.

A reagent 31 containing a surfactant, an RMA (ribonucleic acid) remover, and a fluorescent dye/pigment is accommodated on the bottom, of the internal space 30*c* in a state where the reagent is dried or freeze-dried. When a tissue which is to be subjected to the cell isolation process, and a cell treatment solution (liquid) are loaded into the internal space 30*c*, the reagent 31 dissolves in the cell treatment solution. Preferably, a solution in which the osmotic pressure is equal to that of a living body, such as PBS (phosphate buffer solution) is used as the cell treatment solution. In parallel with a below-described cell isolation process by stirring, nuclei isolation of tissue cells by the surfactant, RNA removal by the RNA remover, and staining of isolated DNA cell nuclei by the fluorescent dye/pigment can be performed. This enables that, after recovery by the cell pre-processing apparatus 3, measurement by the flow cytometer 5 or the like is performed. Therefore, a rapid diagnosis can be realized.

Next, the contents of the cell isolation process in which the thus configured cell isolation device 4 is used, and which is performed by the cell, pre-processing apparatus 3 will be described.

A lid 12 which is disposed in the cell pre-processing apparatus 3, and which is vertically slidable is opened, and a bottom portion of the container 30 is inserted into a positioning hole 13 to support the container 30. An upper end portion of the cell isolation device 4 is connected to a lower end portion of a nozzle 14 of the cell pre-processing apparatus 3. Specifically, a passage of the nozzle 14 and the passage of the lid member 23 communicate with each other in an air- and liquid-tight manner through an adequate engagement structure. When the lid 12 of the cell pre-processing apparatus 3 is closed, the operation of the cell isolation process is started, in the following procedure.

Although the detail is not shown, the cell pre-processing apparatus 3 includes a pump mechanism which is connected to the nozzle 14. Then, a controller of the cell pre-processing apparatus 3 controls the pump mechanism based on stirring conditions (stirring intensity, repetition number, duration, and the like) which are set by the user, to form a pressurized state and a depressurized state. In the pressurized state, air is blown out from the nozzle 14, and, in the depressurized state, air is sucked through the nozzle 14.

By performing the pipetting process in which a pressurized state and a depressurized state are repeatedly formed, the tissue and the cell treatment solution (containing the reagent 31) in the container 30 can be stirred by means of the pipette member 20 connected to the nozzle 14.

In a state where the depressurized condition is formed by the cell pre-processing apparatus 3, a predetermined suction force acts on the pipette member 20, and the cell treatment solution in the container 30 is sucked into the pipette member 20. Part of the cell treatment solution is raised in the passage, and the tissue is attracted to the tip end (opening 21b) of the pipette member 20. At this time, part of the tissue is smashed by collision with the tip end of the pipette member 20.

In a state where the pressurised state is formed by the cell pre-processing apparatus 3, a predetermined pressure is applied to the pipette member 20, and the cell treatment solution in the passage is elected from the opening 21b to be returned to the internal space 30c of the container 30. At this time, the tissue which is attracted to the opening 21b is returned into the cell treatment solution while part of the tissue is smashed by shock caused by the ejection.

By repeating the above-described suction and ejection processes, the tissue is gradually finely smashed to enter a minced state. When the stirring process is performed for a predetermined time period, a suspending solution containing isolated cells can be obtained. In this process, nuclei of cells are broken, and chromosomes therein are stained so as to respond to fluorescence. The fluorescent dye enters between the double helix of DNA. Therefore, the amount of the entering dye is different depending on the size of DNA. Usually, chromosomes of cancer cells are larger than those of normal cells, and hence cancer cells are larger in amount of dyes which are contained as a result of the coloring process, than normal cells.

The isolated cells are used in a pathological analysis. In addition to the isolated cells, however, unwanted minced tissue pieces are suspended in the suspending solution. In order to use only the isolated cells in the analysis, a step of filtering out tissue pieces which are larger than the isolated cells is necessary. Therefore, the cell pre-processing apparatus 3 causes a suction force which is larger than that in the stirring process, to act on the pipette member 20 while the cell isolation device 4 is kept connected to the nozzle 14.

This causes the suspending solution in the container 30 to be sucked into the pipette member 20 to be raised through the passage. When the cell pre-processing apparatus 3 continues the section, the suspending solution reaches the filter 22. When the suspending solution passes through the filter 22, unwanted tissue pieces are filtered out, so that a cell suspension containing desired isolated cells is obtained. When the sucking operation is further continued, the cell suspension is recovered to the cell pre-processing apparatus 3, and then used in an analyzing process such as a fluorescence analysis by using the flow cytometer 5.

Next, a process of acquiring a histogram showing fluorescence intensities (histogram acquiring step) performed by the flow cytometer 5 will be described.

By using the cell suspension, the flow cytometer 5 measures cells which are isolated and nuclear stained, and obtains a scattergram (not shown) in which relationships of related variables are displayed on a plane, from the peak value of a fluorescent signal at each event, and an integrated value. An adequate gating process is performed on the scattergram to obtain a histogram of integrated values of the fluorescence intensity from events which seem to be a single cell. The histogram is displayed on a display (for example, an LCD) of the PC 6. As described above, the flow cytometer 5 functions as a measurer which measures the nuclear stained, cells (cell number), and a histogram acquirer which acquires a fluorescence intensity histogram by using measurement results of the measurer.

Figure 3:
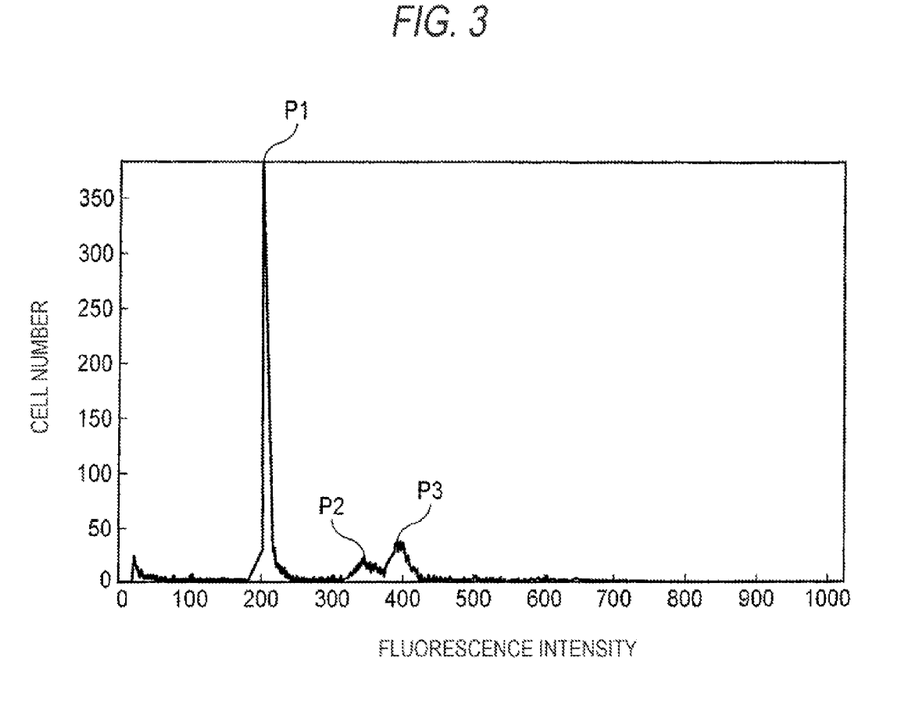
FIG. 3 is a view showing an example of a fluorescence intensity histogram acquired by a flow cytometer.

FIG. 3 shows an example of the acquired histogram. The cell suspension is flown through the flow cytometer 5, and irradiated with laser light. Since cells contain a fluorescent dye as a result of the coloring process, the cells exhibit different light absorptances, and their fluorescence intensities with respect to the laser light are different from one another. The abscissa of the histogram indicates the fluorescence intensity, i.e., the amount of dyes contained in DNA or the size of DNA. The waveform of the histogram is different depending on the number of contained normal DNAs or that, of contained cancerous DNAs.

In FIG. 3, P1 indicates a peak due to groups of G0/G1 phase cells, P2 indicates a peak due to cell groups of DNA Aneuploidy indicating tumor cells which are different in amount of DNA from normal cells, and P3 indicates a peak due to groups of G2/M phase cells. Data of the fluorescence intensity histogram obtained by the flow cytometer 5 are transmitted to the PC (analysis controller) 6 constituting the cell analyzing apparatus 2.

Next, the frequency analysis (frequency analyzing step) and determination of cancer cells (determining step) which are performed by the analysis controller 6 will be described.

The analysis controller 6 has a function of frequency analyzing the data of the histogram acquired by the flow cytometer 5. The analysis controller 6 has a further function of performing a cancer cell determining process in which, based on a result of the frequency analysis, it is determined whether the tissue to be analyzed contains cancer cells or not.

Figure 4:
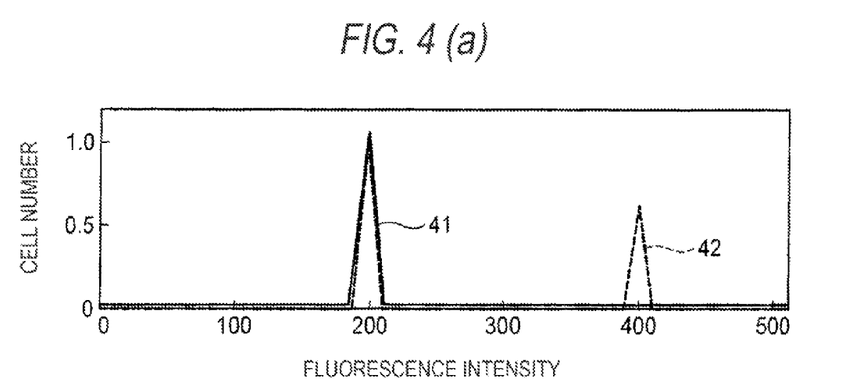
FIG. 4(a) shows histograms.
FIG. 4(b) shows a result of a frequency analysis of the histograms.
Figure 5:
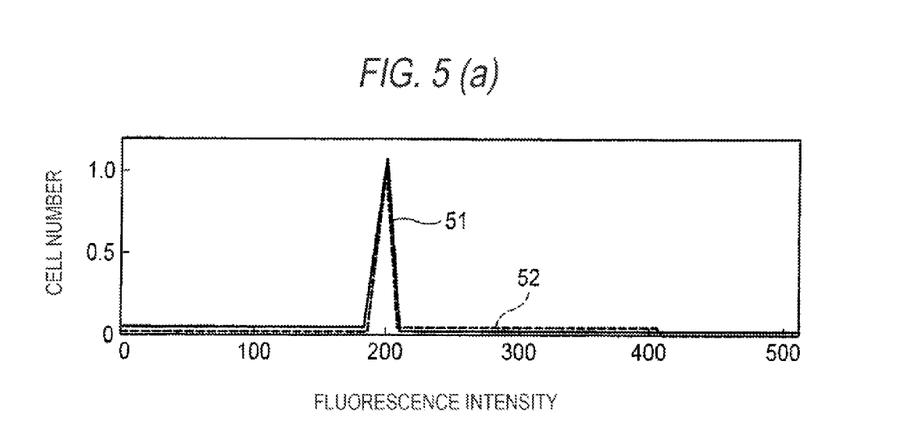
FIG. 5(a) shows histograms.
FIG. 5(b) shows a result of a frequency analysis of the histograms.
Figure 6:
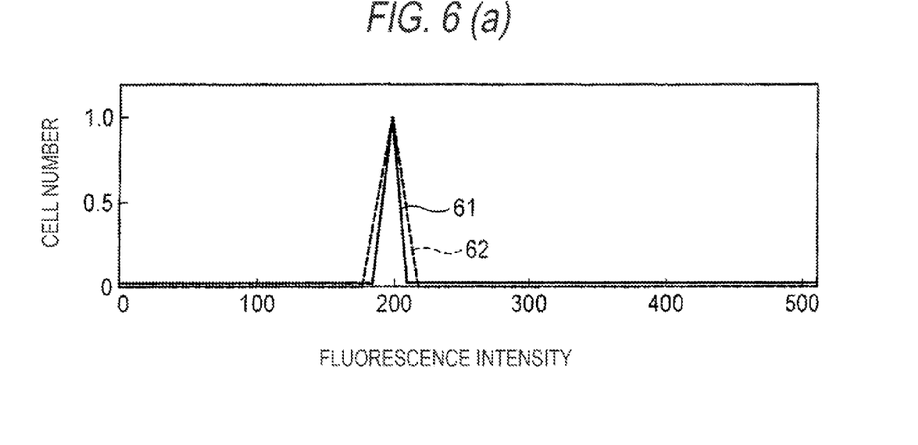

FIGS. 4(a) to 6(b) show histograms of three characteristic types of cancerous cells or Aneuploidy, Spread, and Atypical. FIGS. 4(a), 5(a) and 6(a) show the histogram, indication, and FIGS. 4(b), 5(b) and 6(b) show waveforms which are obtained by frequency analyzing the histograms. In the frequency analysis, a Fast Fourier Transform (FFT) is applied to the data.

In FIG. 4(a), first, the line 41 is a histogram of normal cells, and the line 42 is a histogram of cancer (Aneuploidy) cells. In the histogram 42 of cancer (Aneuploidy) cells, two peaks appear, and one of the peaks appears in the G2/M phase. In both the normal cells and the cancer cells, the measurement sample number was 1,000. In FIGS. 4(a) to 6(b), in order to facilitate comparisons between the characteristics of the normal and cancer cells, and between the figures, the ranges of the ordinates are normalized to be identical.

In FIG. 4(b), the line 43 shows a result of the FFT process performed on the histogram 41 of normal cells, and the line 44 shows a result of the FFT process performed on the histogram 42 of cancer (Aneuploidy) cells. A plurality of obvious ripples appear in the FFT pattern of the line 44. The ADC (Area Under the Curve) of the line 43 is 52 (Normal AUC), and that of the line 44 is 35 (Aneuploidy AUC). Namely, the AUC of cancer (Aneuploidy) cells is smaller.

In FIG. 5(a), then, the line 51 is a histogram of normal cells, and the line 52 is a histogram of cancer (Spread) cells. In the histogram 52 of cancer (Spread) cells, a relatively large number of cells appear in the S phase. In the normal cells, the measurement sample number was 1,000, and, in the cancer cells, the measurement sample number was 1,738.

in FIG. 5(b), the line 53 shows a result of the FFT process performed on the histogram 51 of normal cells, and the line 54 shows a result of the FFT process performed on the histogram 52 of cancer (Spread) cells. In the FFT pattern of the line 54, steep attenuation 55 in the direction toward a higher frequency occurs in a low spatial frequency (the left side of the figure). The AUC of the line 53 is 52 (Normal AUC), and that of the line 54 is 29 (Spread AUC). Namely, the AUC of cancer (Spread) cells is smaller.

In FIG. 6(a), then, the line 61 is a histogram of normal cells, and the line 62 is a histogram of cancer (Atypical) cells. In the histogram 62 of cancer (Atypical) cells, a peak appears in the G0/G1 phase. However, the peak has a shape which is different from the histogram of Diploidy. In the normal cells, the measurement sample number was 1,000, and, in the cancer cells, the measurement sample number was 2,000.

In FIG. 6(b), the line 63 shows a result of the FFT process performed on the histogram 61 of normal cells, and the line 64 shows a result of the FFT process performed on the histogram 62 of cancer (Atypical) cells. The AUC of the line 63 is 52 (Normal AUC), and that of the line 64 is 26 (Atypical AUC). Namely, the AUC of cancer (Atypical) cells is smaller.

Next, results of cell analysis which was performed according to the cell analyzing method of the presently disclosed subject matter on tissue extracted for treatment from patients (26 patients) with progressive colorectal cancer are shown below.

Figure 7:
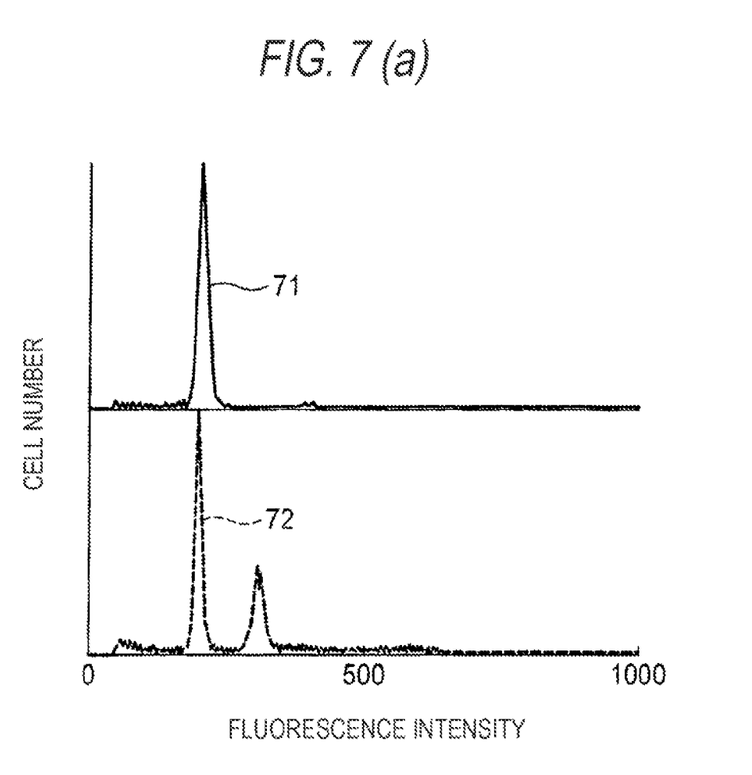
FIG. 7(a) shows histograms.
FIG. 7(b) shows histograms in which the cell number of the ordinate of FIG. 7(a) is normalized.
FIG. 7(c) shows a result of a frequency analysis of the histograms of FIG. 7(b).
Figure 8:
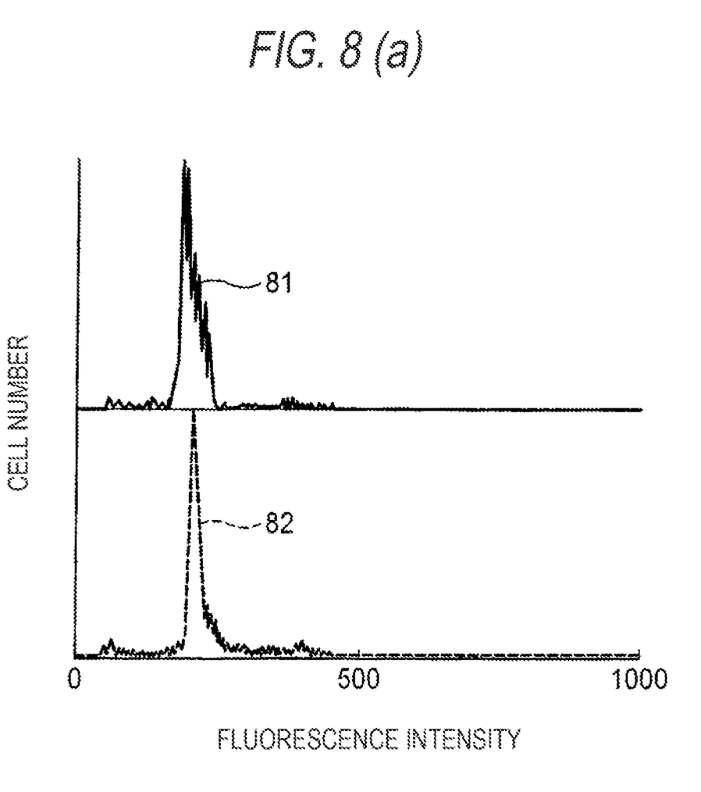
FIGS. 8(a), 8(b) and 8(c) are views which show an example of a result of a process of analyzing cancer cells, and in which FIG. 8(*a*) shows histograms, FIG. 8(*b*) shows histograms in which the cell number of the ordinate of FIG. 8(*a*) is normalised, and FIG. 8(*c*) shows a result of a frequency analysis of the histograms of FIG. 8(*b*).
Figure 9:
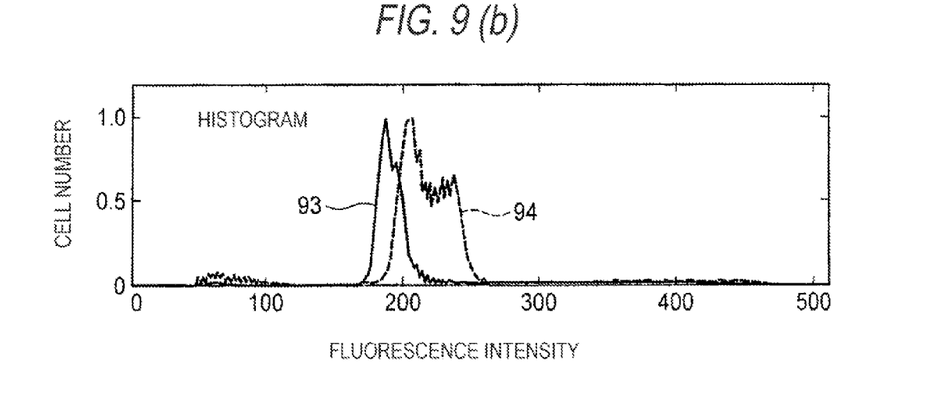
Figure 9A:
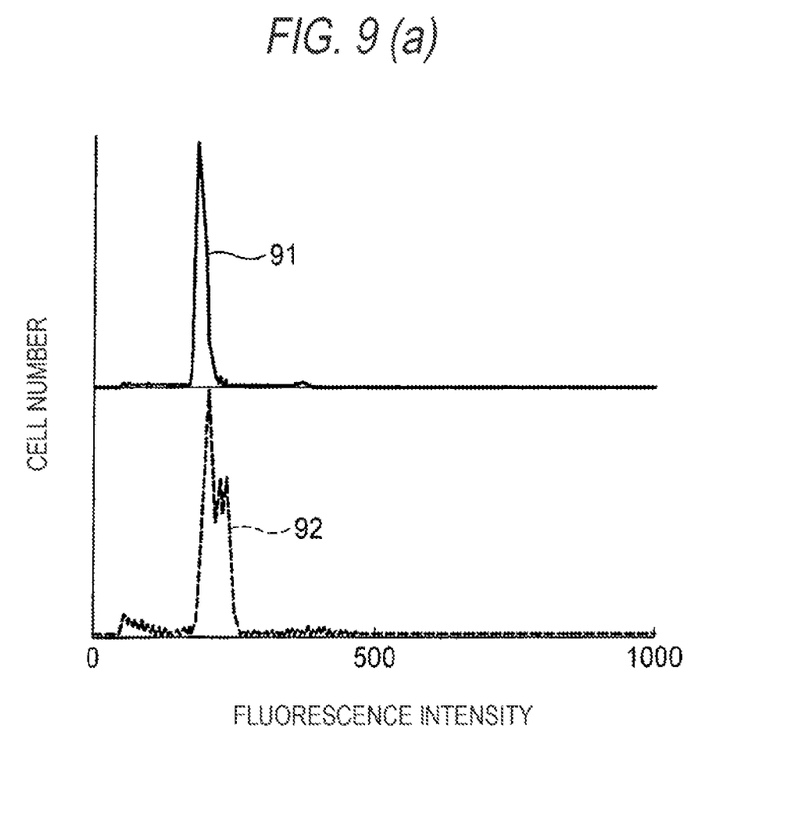

FIGS. 7(a) to 9(c) show histograms and FFT patterns of the above-described three characteristic types (Aneuploidy, Spread, and Atypical) in the 26 samples which were subjected to the cell analysis. FIGS. 7(a), 8(a) and 9(a) show histograms of normal cells (upper side) and cancer cells (lower side), FIGS. 7(b), 8(b) and 9(b) show histograms in which the ordinates of the histograms of FIGS. 7(a), 8(a) and 9(a) are normalized, and FIGS. 7(c), 8(c) and 9(c) show results of FFT processes performed on the histograms.

FIGS. 7(a), 7(b) and 7(c) show results of cell analysis which was performed on tissue extracted from patients with Aneuploidy cancer. In FIG. 7(a), the line 71 is a histogram of normal cells, and the line 72 is a histogram of cancer (Aneuploidy) cells. The abscissa indicates the fluorescence intensity, and the ordinate indicates the cell number. In FIG. 7(b), the two histograms shown in FIG. 7(a) are shown in the same graph, the line 73 is the histogram of normal cells, and the line 74 is the histogram of cancer (Aneuploidy) cells. In order to facilitate the comparison, the cell numbers of the ordinates are normalized and unified. In FIG. 7(c), results of FFT processes performed on the histograms shown in FIG. 7(b) are shown, the line 75 is an FFT pattern of normal cells, and the line 76 is an FFT pattern of cancer (Aneuploidy) cells.

As shown in FIG. 7(b), two peaks appear in the histogram 74 of cancer (Aneuploidy) cells. In the FFT pattern 76 (FIG. 7(c)) which is obtained by performing the FFT process on the histogram, a plurality of obvious ripples appear in the spatial frequency. The AUC (Area Under the Curve) of the FFT pattern 75 is 28 (Normal AUC), and that of the FFT pattern 76 is 21 (Aneuploidy AUC). Namely, the AUC of cancer (Aneuploidy) cells is smaller. As described above, when comparing the results of the FFT processes performed on the histograms with each other, distinct differences appear in the FFT patterns and their AUCs.

FIGS. 8(a), 8(b) and 8(c) show results of cell analysis which was performed on tissue extracted from patients with Spread cancer. In FIG. 8(a), the line 81 is a histogram of normal cells, and the line 82 is a histogram of cancer (Spread) cells. In FIG. 8(b), the two histograms shown in FIG. 8(a) are shown in the same graph, the line 83 is the histogram of normal cells, and the line 84 is the histogram of cancer (Spread) cells. In FIG. 8(c), results of FFT processes performed on the histograms shown in FIG. 8(b) are shown, the line 85 is an FFT pattern of normal cells, and the line 86 is an FFT pattern of cancer (Spread) cells.

As shown in FIG. 8(c), in the FFT pattern 86 which is obtained by performing the FFT process on the histogram 84 of cancer (Spread) cells, steep attenuation 87 (enclosed by the broken line) in the direction toward a higher frequency occurs in a low spatial frequency range (the left side of the graph). The AUC of the FFT pattern 85 is 24 (Normal AUC), and that of the FFT pattern 86 is 21 (Spread AUC). Namely, the AUC of cancer (Spread) cells is smaller. As described above, when comparing the results of the FFT processes performed on the histograms with each other, distinct differences appear in the FFT patterns and their AUCs.

FIGS. 9(a), 9(b) and 9(c) show results of cell analysis which was performed on tissue extracted from patients with Atypical cancer. In FIG. 9(a), the line 91 is a histogram of normal cells, and the line 92 is a histogram of cancer (Atypical) cells. In FIG. 9(b), the two histograms shown in FIG. 9(a) are shown in the same graph, the line 93 is the histogram of normal cells, and the line 94 is the histogram of cancer (Atypical) cells. In FIG. 9(c) of the figure, results of FFT processes performed on the histograms shown in FIG. 9(b) are shown, the line 95 is an FFT pattern of normal cells, and the line 96 is an FFT pattern of cancer (Atypical) cells.

As shown in FIG. 9(c), the AUC of the FFT pattern 95 is 29 (Normal AUC), and that of the FFT pattern 96 is 17 (Atypical AUC). Namely, the AUC of cancer (Atypical) cells is smaller. As described above, when comparing the results of the FFT processes performed on the histograms with each other, distinct differences appear in the FFT patterns and their AUCs.

Figure 10:
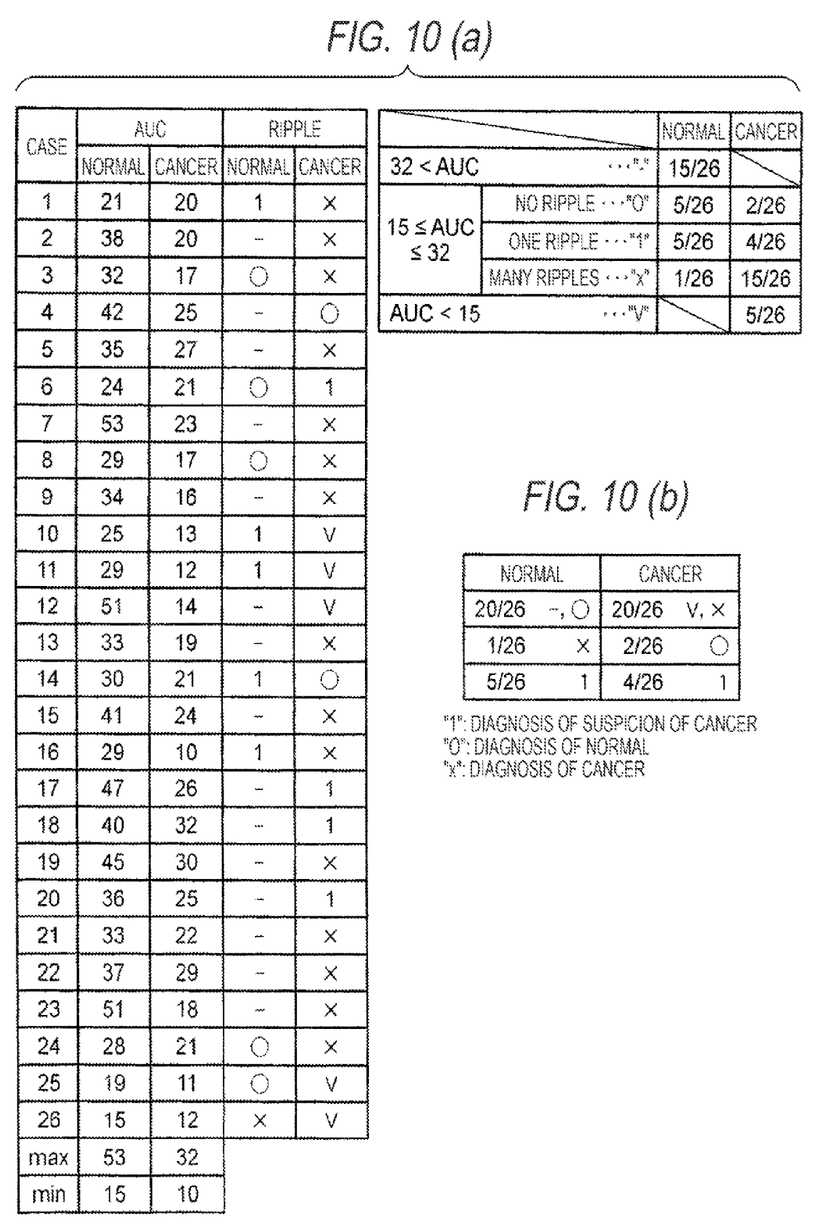

FIG. 10(a) and FIG. 10(b) show tables which show measurement data of the AUC (Area Under the Curve) and ripple of an FFT pattern of the patients (26 patients) with colorectal cancer, and diagnosis results based on the data.

In FIG. 10(a), Cases 1 to 26 of the first column indicate the patients (26 patients), "AUC Normal" of the second column indicates the area under the curve of an FFT pattern which is obtained by performing the FFT process on a histogram of normal cells of tissue extracted from a patient (living body), "AUC Cancer" of the third column indicates the area under the curve of an FFT pattern which is obtained by performing the FFT process on a histogram of cancer cells of tissue extracted from a living body, "Ripple Normal" of the fourth column indicates whether the FFT pattern which is obtained by performing the FFT process on the histogram of normal cells ripples or not, and "Ripple Cancer" of the fifth column indicates whether the FFT pattern which is obtained by performing the FFT process on the histogram of cancer cells ripples or not.

As shown in "AUC Normal" of the second column, the maximum value (max) of the AUCs of normal cells was 53, and the minimum value (min) was 15. As shown in "AUC Cancer" of the third column, the maximum value (max) of the AUCs of cancer cells was 32, and the minimum value (min) was 10. From these results, when the AUC of the measured cells is smaller than 15 which is the minimum value of the AUCs of normal cells, it was determined that the cells are cancer cells. When the AUC of the measured cells is larger than 32 which is the maximum value of the AUCs of cancer cells, it was determined that the cells are normal cells. The minimum value of 15 of the AUCs of normal cells, and the maximum value of 32 of the AUCs of cancer cells are examples of the threshold described in the appended claims.

In "Ripple Normal" and "Ripple Cancer" of the fourth and fifth columns, with respect to the determination results based on the AUC value, a diagnosis of normal cells is indicated by "–" and that of cancer cells is indicated by "V". In "Ripple Normal" of the fourth column, Cases 2, 4, 5, 7, 9, 12, 13, 15, and 17 to 23 are "–". Namely, 15/26 can be determined to be normal cells, by a diagnosis based on the AUC value. In "Ripple Cancer" of the fifth column, Cases 10 to 12, 25, and 26 are "V". Namely, 5/26 can be determined to be cancer cells, by a diagnosis based on the AUC value.

With respect to the cases where the area under the curve of an FFT pattern is 15≤AUC≤32, a determination cannot be made based only on the AUC, and therefore a determination is made based on the existence/nonexistence of Ripple of the FFT pattern in the following manner. Namely, the area under the curve of an FFT pattern and the existence/nonexistence of Ripple of the FFT pattern are combined with each other, and a determination whether the cells to be analysed are cancer cells or not is comprehensively made.

In "Ripple Normal" of the fourth column, 11 cases or Cases 1, 3, 6, 8, 10, 11, 14, 16, and 24 to 26 are in the range of 15≤AUC≤32. In "Ripple Cancer" of the fifth column, 21 cases or Cases 1 to 9 and 13 to 24 are in the range of 15≤AUC≤32. Among these cases, the cases where a ripple (s) does not exist in an FFT pattern are indicated by "○", those where one ripple exists in an FFT pattern are indicated by "1", and those where a large number of ripples exist in an FFT pattern are indicated by "×".

In "Ripple Normal" of the fourth column. Cases 3, 6, 8, 24, and 25 are "○" (5/26), Cases 1, 10, 11, 14, and 16 are "1" (5/26), and Case 26 is "×" (1/26). In "Ripple Cancer" of the fifth column, Cases 4 and 14 are "○" (2/26), Cases 6, 17, 18, and 20 are "1" (4/26), and Cases 1 to 3, 5, 7 to 9, 13, 15, 16, 19, and 21 to 24 are "×" (15/26).

In FIG. 10(b), the diagnosis results based on the determinations of Cases 1 to 26 are classified into three categories: TRUE, ERROR, and Suspicion.

The symbols used in "Ripple Normal" and "Ripple Cancer" of the fourth and fifth columns in FIG. 10(a) are defined as follows: "–" and "○" indicate a diagnosis of normal, "1" indicates a diagnosis of suspicion of cancer, and "V" and "×" indicate a diagnosis of cancer. With respect to normal cells extracted, from living bodies (26 patients), diagnosis results were obtained in which 20/26 are TRUE, 1/26 is ERROR, and 5/26 are Suspicion. With respect to cancer cells extracted from living bodies (26 patients), diagnosis results were obtained in which 20/26 are TRUE, 2/26 are ERROR, and 4/26 are Suspicion. Namely, it was confirmed that, with respect to normal, cells, a diagnosis of cancer cells is made with a probability of 1/26 (3.8%). Furthermore, it was confirmed that, with respect to cancer cells, a diagnosis of normal cells is made with a probability of 2/26 (7.7%).

From the above, the apparatus and method of analyzing cells of the presently disclosed subject matter attain the following functions and effects.

A frequency analysis (FFT process) is performed on a histogram snowing fluorescence intensities of normal and cancer cells which are stained, and the difference/features of normal and cancer cells are clarified by FFT patterns. In the presently disclosed subject matter, the existence/nonexistence of cancer cells is determined based on a result of the analysis. Therefore, cancerous cells can be distinguished surely, accurately, and rapidly. According to the configuration, separation of cells from an extracted tissue and staining of the cells require about six minutes, and acquisition of histograms from the stained cells and FFT patterns of the histograms requires about four minutes. Namely, the existence/nonexistence of cancer cells can be determined only for about ten minutes.

The waveform of the histogram appears in different manners depending on the kind of the extracted cancer cells (Aneuploidy, Spread, or Atypical). When an FFT is applied to the histogram, its features distinctively appear. In the presently disclosed subject matter therefore, the histogram is frequency-analyzed, the area under curve (AUC) of a waveform obtained from the result of the analysis is compared with a predetermined threshold (for example, the value of the AUC obtained from normal cells) to determine the existence/nonexistence of cancer cells. Consequently, cancerous cells can be distinguished more surely, accurately, and rapidly.

Moreover, the existence/nonexistence of cancer cells is determined depending on whether the waveform which is obtained by performing the FFT process on the histogram ripples in the spatial frequency or not. Therefore, cancerous cells can be distinguished more surely, accurately, and rapidly. For example, Aneuploidy cancer cells can foe diagnosed more clearly.

Furthermore, the existence/nonexistence of cancer cells is determined depending on whether the waveform which is obtained by performing the FFT process on the histogram has steep attenuation in the direction toward a higher frequency in a low spatial frequency region or not. Therefore, cancerous cells can be distinguished more surely, accurately, and rapidly. For example, Spread and Atypical cancer cells can be diagnosed more clearly.

In the example of FIGS. 10(a) and 10(b), a determination whether the cells to be analyzed are cancer cells or not is comprehensively made while combining the size of the area under the curve of an FFT pattern with the existence/nonexistence of Ripple of the FFT pattern. Further considering whether steep attenuation in the direction toward a higher frequency in a low spatial frequency region of the FFT pattern exists or not, the determination whether the cells to be analyzed are cancer cells or not may be comprehensively made, whereby the accuracy of the diagnosis can be improved.

According the determining method in the presently disclosed subject matter based on a histogram and a result of frequency analysis, a new patient can be diagnosed based on analysis sample data which have been acquired. Therefore, it is possible to rapidly and correctly distinguish whether the tissue to be analyzed contains cancer cells or not, without newly excising and extracting normal cells. The cell analysis may be applied also to breast cancer, a lymph node, bile duct, adenoma, and the like.

According to an aspect of the presently disclosed subject matter, a frequency analysis is performed on a histogram showing fluorescence intensities of normal and cancer cells which are stained, and the existence/nonexistence of cancer cells is determined based on a result of the analysis. Therefore, the difference between normal and cancer cells becomes clear, and hence cancerous cells can be distinguished more accurately and rapidly.

What is claimed is:

1. A cell analyzing apparatus comprising:
a histogram acquirer which is configured to perform measurement of a number of nuclear stained cells, and which, by using a result of the measurement, is configured to acquire a histogram indicating a fluorescence intensity; and
an analysis controller which is configured to apply frequency analysis on data of the histogram acquired by the histogram acquirer, and which is configured to determine existence/nonexistence of cancer cells based on a result of the frequency analysis, wherein the frequency analysis is a Fast Fourier Transform applied to the data of the histogram relating to the fluorescence intensity and the number of nuclear stained cells, and
wherein the analysis controller determines the existence/nonexistence of the cancer cells by comparing an area under a curve of a waveform which is obtained from the result of the frequency analysis, with a predetermined threshold.

2. A cell analyzing apparatus comprising:
a histogram acquirer which is configured to perform measurement of a number of nuclear stained cells, and which, by using a result of the measurement, is configured to acquire a histogram indicating a fluorescence intensity; and
an analysis controller which is configured to apply frequency analysis on data of the histogram acquired by the histogram acquirer, and which is configured to determine existence/nonexistence of cancer cells based on a result of the frequency analysis,
wherein the frequency analysis is a Fast Fourier Transform applied to the data of the histogram relating to the fluorescence intensity and the number of nuclear stained cells, and
wherein the analysis controller determines the existence/nonexistence of the cancer cells depending on whether or not a waveform which is obtained from the result of the frequency analysis ripples in a spatial frequency.

3. A cell analyzing apparatus comprising:
a histogram acquirer which is configured to perform measurement of a number of nuclear stained cells, and which, by using a result of the measurement, is configured to acquire a histogram indicating a fluorescence intensity; and
an analysis controller which is configured to apply frequency analysis on data of the histogram acquired by the histogram acquirer, and which is configured to determine existence/nonexistence of cancer cells based on a result of the frequency analysis,
wherein the frequency analysis is a Fast Fourier Transform applied to the data of the histogram relating to the fluorescence intensity and the number of nuclear stained cells, and
wherein the analysis controller determines the existence/nonexistence of the cancer cells depending on whether or not a waveform which is obtained from the result of the frequency analysis steeply attenuates in a direction toward a higher frequency in a low spatial frequency region.

4. A cell analyzing apparatus comprising:
a histogram acquirer which is configured to perform measurement of a number of nuclear stained cells, and which, by using a result of the measurement, is configured to acquire a histogram indicating a fluorescence intensity; and
an analysis controller which is configured to apply frequency analysis on data of the histogram acquired by the histogram acquirer, and which is configured to determine existence/nonexistence of cancer cells based on a result of the frequency analysis,
wherein the frequency analysis is a Fast Fourier Transform applied to the data of the histogram relating to the fluorescence intensity and the number of nuclear stained cells, and
wherein the analysis controller comprehensively determines a comparison between an area under a curve of a waveform which is obtained from the result of the frequency analysis, and a predetermined threshold, existence/nonexistence of a ripple in a spatial frequency, and existence/nonexistence of steep attenuation in a direction toward a higher frequency in a low spatial frequency region, thereby determining the existence/nonexistence of the cancer cells.

5. The cell analyzing apparatus according to claim 1, wherein the predetermined threshold is a value of the area under the curve, which is obtained from normal cells of a living body.

6. A cell analyzing method comprising:
using a histogram acquirer to perform measurement of a number of nuclear stained cells, and, by using a result of the measurement, acquiring a histogram indicating a fluorescence intensity;
using an analysis controller to apply frequency analysis on data of the acquired histogram; and to determine existence/nonexistence of cancer cells based on a result of the frequency analysis,
wherein the frequency analysis is a Fast Fourier Transform applied to the data of the histogram relating to the fluorescence intensity and the number of nuclear stained cells, and
wherein the analysis controller determines the existence/nonexistence of the cancer cells by comparing an area under a curve of a waveform which is obtained from the result of the frequency analysis, with a predetermined threshold.

* * * * *

UNITED STATES PATENT AND TRADEMARK OFFICE
CERTIFICATE OF CORRECTION

PATENT NO.        : 9,448,228 B2                                                Page 1 of 1
APPLICATION NO.   : 13/917534
DATED             : September 20, 2016
INVENTOR(S)       : Takeda et al.

It is certified that error appears in the above-identified patent and that said Letters Patent is hereby corrected as shown below:

In the Specification

Column 4, Line 56: please delete "RMA" and replace it with -- RNA --

Column 7, Line 23: please delete "ADC" and replace it with -- AUC --

Signed and Sealed this
Third Day of January, 2017

Michelle K. Lee
*Director of the United States Patent and Trademark Office*